United States Patent
Lai et al.

(10) Patent No.: US 7,381,430 B2
(45) Date of Patent: Jun. 3, 2008

(54) PHARMACEUTICAL COMPOSITION COMPRISING A COMBINATION OF CHINESE TRADITIONAL MEDICINES

(75) Inventors: Zuqin Lai, Beijing (CN); Xuhuai Huang, Beijing (CN)

(73) Assignee: Beijing Qijieyuan Pharmaceutical Technology Development Co., Ltd., Beijing (CN)

( * ) Notice: Subject to any disclaimer, the term of this patent is extended or adjusted under 35 U.S.C. 154(b) by 0 days.

(21) Appl. No.: 10/599,758

(22) PCT Filed: May 24, 2004

(86) PCT No.: PCT/CN2004/000522

§ 371 (c)(1),
(2), (4) Date: Oct. 6, 2006

(87) PCT Pub. No.: WO2005/097148

PCT Pub. Date: Oct. 20, 2005

(65) Prior Publication Data

US 2007/0202201 A1      Aug. 30, 2007

(30) Foreign Application Priority Data

Apr. 9, 2004   (CN)   ......................... 2004 1 0030849

(51) Int. Cl.
*A01N 65/00* (2006.01)
*A61K 36/48* (2006.01)
*A61K 36/899* (2006.01)
*A61K 36/16* (2006.01)

(52) U.S. Cl. .................. 424/725; 424/757; 424/750; 424/752

(58) Field of Classification Search ................ None
See application file for complete search history.

(56) References Cited

FOREIGN PATENT DOCUMENTS

CN            1215601            5/1999

OTHER PUBLICATIONS

Simon et al, www.thelancet.com, seminar 368: 489-504, 2006.*
Mirken (AIDS Treat News. Apr. 21, 2000;(341): 4-6).*

* cited by examiner

*Primary Examiner*—Patricia Leith
*Assistant Examiner*—Qiuwen Mi
(74) *Attorney, Agent, or Firm*—J.C. Patents

(57) ABSTRACT

The present invention provides a pharmaceutics of traditional Chinese medicine and preparation method thereof, said pharmaceutics is prepared from Geranium, Root of Membranous Milkvetch, Herba Solani Nigri, Honeysuckle Flower, Flower of Common Bombax, Fruit of Belleric Terminalia, Herba Hedyotis Diffusae, Pomegranate Rind, Radix Oryzae, Fructus Trapae. The pharmaceutics of the present invention can clear away heat and toxic materials, activate blood circulation and supplementing qi, raise bacteria count of CD4 lymphocyte of infected person of AIDS and subject of AIDS (CD4 lymphocyte 100-400 unit/mm$^3$), and ameliorate hypodynamia, alopecia, anorexia, diarrhea, and status of activity function.

3 Claims, No Drawings

PHARMACEUTICAL COMPOSITION COMPRISING A COMBINATION OF CHINESE TRADITIONAL MEDICINES

FIELD OF THE INVENTION

The present invention relates to a traditional Chinese medicine (TCM) preparation for treating Acquired Immune Deficiency Syndrome (AIDS) and its preparation method. The preparation is a multitarget drug, which not only can improve the immunological function, but also has antivirus, anti-infection and anti-tumor effects. When AIDS patients of early stage take the preparation of the present invention, the advancement of AIDS can be controlled or reversed; for AIDS patients of medium stage, it can prevent further damage of immunologic system, recover and reinforce the immunologic functions; for AIDS patients of late stage, the preparation can control the development of complications, the ingredients of the preparation will coordinate to achieve the goal of strengthening healthy Qi to eliminate pathogens.

BACKGROUND OF THE INVENTION

Though clinical manifestations of AIDS are complicated, the pathogenic reasons are limited in two aspects of internal and exogenous causes. Exogenous causes generally are evil, toxin, skin diseases or infections, while internal causes are the extreme weaknesses of entrails, Qi and blood; but exogenous evils do the damage mainly because there are internal weaknesses in the first place, and exogenous evils exert effects through internal causes. Phlegm retention and congestion are the pathologic outputs formed by functional disorders of entrails, Qi and blood induced by AIDS, at the same time they also become pathologic factors to cause the generation of superficial nodules, ulcers and malignant tumors. Because this disease is a general disease, internal factors play the major role in pathopoiesis. Chinese patent No. 97119177.8 discloses a Chinese herbal medicine for treating AIDS, which mainly contains Snakegourd root, Bitter melon, Dandelion, Chinese pulsatilla root, Liquorice Root, Lespedeza cuneata, Root of Membranous Milkvetch, Calculus equi, Flos lonicerae, Dyers woad leaf, Baical skullcap root, Radix ginseng silvestris, Cornu antelopes, and Oreocharis benthamii var. In addition, it also contains Green Basilisk, Shenshandiaoyuncao, Cavalerie mosla herb (mini), and Glabrousleaf pittosporum leaf (maxi). This Chinese herbal medicine for treating AIDS is prepared by rumination technique to obtain the pure natural elites in plants and animals, the obtained materials are extracted and refined by high technological equipment and advanced techniques. This drug can inhibit the multiply of human immunodeficiency virus (HIV) and improve the capacity of human antibodies, increase the immunological functions of adrenal cortex, genital gland and cells. But the therapeutic effect of this drug is not as good as desired, and its preparation method is not suitable for large scale industrial production. Therefore, there is a need for a new and effective Chinese herbal medicine preparation for treating AIDS.

SUMMARY OF THE INVENTION

The aim of the invention is to provide a Chinese medicine preparation to treat AIDS, which is a multitarget preparation, and not only can improve the immunological function, but also has antivirus, anti-infection and anti-tumor effects. When AIDS patients of early stage take the drug of the present invention, the drug can control and reverse the development of AIDS; for AIDS patients of medium stage, it can prevent further damage of immunologic system, recover and improve the immunologic functions; for AIDS patients of late stage, the drug can control the development of complications, the ingredients of the drug will coordinate to achieve the goal of strengthening healthy Qi to eliminate pathogens.

The aim of the invention is realized by providing a Chinese medicine preparation for treating AIDS, characterized in that the preparation is prepared according to the following weight proportions of raw materials:

| | |
|---|---|
| Geranium | 120-150 |
| Root of Membranous Milkvetch | 120-150 |
| Herba Solani Nigri | 120-200 |
| Honeysuckle Flower | 120-200 |
| Flower of Common Bombax | 60-100 |
| Fruit of Belleric Terminalia | 40-60 |
| Herba Hedyotis Diffusae | 80-150 |
| Pomegranate Rind | 40-60 |
| Radix Oryzae | 150-200 |
| Fructus Trapae | 80-150. |

The present invention also provides a preparation method of a Chinese medicine tablet for treating AIDS, using Geranium, Honeysuckle Flower, Pericarpium Trichosanthis, Root of Chinese Thorowax, Herb of Chinese Mosla, Pomegranate Rind, Root of Membranous Milkvetch, Liquorice Root, Flower of Common Bombax, Stem of Suberect Spatholobus, Safflower, Radix Oryzae, Fruit of Belleric Terminalia, Herba Hedyotis Diffusae, Fructus Trapae, Ginkgo leaf, Purslande herb, Rhizoma picrorhizae, Herba Solani Nigri, Scorpion as raw medicinal materials, and the preparation procedure is as follows:

A. Cut the medicinal materials (Geranium, Root of Chinese Thorowax, Herb of Chinese Mosla, and Honeysuckle Flower) for extracting volatile oils into 2-5 cm pieces, and grind fine powder medicinal material scorpion into fine powders for later use;

B. Extract the medicinal materials for extracting volatile oils for 5 hrs, collect the aqueous solution in another container after distillation, clathrate the volatile oil with cyclodextrin for later use;

C. Add water and decoct twice the rest 15 raw medicinal materials such as Pomegranate Rind, etc. with the gruffs obtained after the volatile oil is extracted in the above step, 10 times of water should be added for the first time and 8 times water for the second time, decoct the mixture 2 hrs for each time. Mix the liquid decocted out and filter (160-180 screen mesh), then mix the filtrate with the abovementioned aqueous solution, concentrate the mixture to a relative density about 1.30 (determined at 50° C.), add clathrate of fine scorpion powder and cyclodextrin, decompress to condense (65° C.~75° C.) till it is dry, grind the obtained substance and prepare powdered extract.

D. Add a proper amount of 16% wet starch to the powdered extract, mix well and add 95% ethanol, make granules through 16 mesh screen, then granulate through 14 mesh screen, dry (lower than 60° C.) and add 1% magnesium stearate, squash to 1000 tablets, and preparation is completed after coated.

In the invention, Honeysuckle Flower is the principal drug which has effects of heat-clearing and detoxicating, tonifying and treating wind evil, and it will not hurt healthy energy. Root of Membranous Milkvetch can benefit Qi to solidify skin, Radix Oryzae can invigorate the spleen and foster the stomach, they are ministerial drugs which can assist the principal drug to promote generation of antibodies, increase the anti-tumor capacity, and activate the functions of T lymphocytes and phagocytes, thus to enhance the immunity activity. After evil toxin invades human body, exhaustion of healthy energy would be induced, and it will cause imbalance of YIN and YANG, QI-blood consumptive disease, excessive diseases and weaknesses, so Geranium, Herba Solani Nigri and Herba Hedyotis Diffusae are chosen to expel wind and activate blood flow, clear heat of upper warmer, and these raw drugs of heat-clearing and detoxicating are adjunctive drugs, which form a detoxicating and expelling pathogen force to assist principal drug to expel evils and toxins. Evils and toxins invade the human body to make the Yin-Yang imbalanced, the spleen and stomach are sluggish to receive food, Flower of Common Bombax, medicine terminalia fruit, Pomegranate Rind and Fructus Trapae are chosen to be messenger drugs to nourish Qi and invigorate spleen, neutralize stomach and check diarrhea, promote the functions of moisture, transportation and transformation of the spleen and stomach, thus to improve appetite, and these present that the spleen and stomach are the source of life in TCM, and they can reinforce healthy energy of human body and disease resistance.

Treating AIDS with Chinese medicine starts from the concept of human body, so in the multitarget drugs in the invention, there are not only drugs to improve immunological functions of human body, but also drugs to work against virus, resist infections and tumors. When AIDS patients of early stage take the drug of the present invention, the drug can control and reverse the advancement of AIDS; for AIDS patients of medium stage, it can prevent the continuous damage of immunologic system, recover and reinforce the immunologic functions; for AIDS patients of late stage, the drug can control the development of complications, ingredients of the drug will coordinate to achieve the goal of strengthening healthy Qi to eliminate pathogens.

From the point of view of the TCM, AIDS is a disease of "asthenia in origin and asthenia in superficiality", the whole course is a process during which the body immunity is gradually destructed, so it is a deficient syndrome. So the heat-clearing and detoxicating drugs of the invention just clear heat but not hurt healthy energy, so there is no violent drug, and they can realize the effects of strengthening body resistance and driving away evil.

DESCRIPTION OF THE PREFERRED EMBODIMENTS

Example 1

A TCM preparation for treating AIDS is prepared according to the following weight proportion:

| | |
|---|---|
| Geranium | 120-150 |
| Root of Membranous Milkvetch | 120-150 |
| Herba Solani Nigri | 120-200 |
| Honeysuckle Flower | 120-200 |
| Flower of Common Bombax | 60-100 |
| Fruit of Belleric Terminalia | 40-60 |
| Herba Hedyotis Diffusae | 80-150 |
| Pomegranate Rind | 40-60 |
| Radix Oryzae | 150-200 |
| Fructus Trapae | 80-150 |

A preparation method of tablets of the invention is as follows:

Take Geranium and Honeysuckle Flower, add water, extract volatile oil by wet distillation for 5 hrs, and collect aqueous solution in another container; clathrate volatile oil with cyclodextrin for later use; decoct the gruffs obtained after extracting the volatile oil with water for two times, add 10 times water for the first time and 8 times water for the second time, and the decoction duration is 2 hrs for each time. Mix the decocted liquids and filter them, then mix the filtrate with the abovementioned aqueous solution and concentrate the mixed liquid to a relative density of 1.30 (determined at 50° C.), add clathrate of cyclodextrin, decompress to condense (65° C.~75° C.) and dry the mixture, grind and add a proper amount of starch, mix them well, granulate with ethanol and dry the granules (lower than 60° C.), add 1% magnesium stearate and squash to 1000 tablets. The weight unit of the above raw materials is gram, the tablet specification is 0.4 g for each tablet which corresponds to 1.79 g crude drug in whole.

Example 2

A TCM preparation for treating AIDS is prepared according to the following weight proportion:

| | |
|---|---|
| Geranium | 180 |
| Root of Membranous Milkvetch | 180 |
| Herba Solani Nigri | 180 |
| Honeysuckle Flower | 180 |
| Flower of Common Bombax | 120 |
| Fruit of Belleric Terminalia | 90 |
| Herba Hedyotis Diffusae | 180 |
| Pomegranate Rind | 90 |
| Radix Oryzae | 300 |
| Fructus Trapae | 180. |

The above raw materials is prepared into tablets by the same method mentioned in Example 1.

Example 3

A TCM preparation for treating AIDS is prepared according to the following weight proportion:

| | |
|---|---|
| Geranium | 120-150 |
| Root of Membranous Milkvetch | 120-150 |
| Herba Solani Nigri | 120-120 |
| Honeysuckle Flower | 120-120 |
| Flower of Common Bombax | 60-100 |
| Fruit of Belleric Terminalia | 40-60 |
| Herba Hedyotis Diffusae | 80-150 |
| Pomegranate Rind | 40-60 |
| Radix Oryzae | 150-200 |
| Fructus Trapae | 80-150 |
| Pericarpium Trichosanthis | 40-60 |
| Root of Chinese Thorowax | 60-100 |
| Herb of Chinese Mosla | 40-60 |
| Liquorice Root | 60-80 |
| Stem of Suberect Spatholobus | 120-150 |
| Safflower | 40-60 |
| Ginkgo leaf | 40-60 |
| Purslande herb | 60-120 |
| Rhizoma picrorhizae | 40-60 |
| Scorpion | 28-40. |

The preparation method of tablets containing the above 20 raw medicinal materials of the invention is as follows:

Grind Scorpion into fine powder; take Geranium, Root of Chinese Thorowax, Herb of Chinese Mosla, Honeysuckle Flower, extract volatile oil for 5 hrs and collect the aqueous solution in another container after distillation; clathrate the volatile oil with cyclodextrin for later use; take the rest 15 raw medicinal materials mentioned above such as Pomegranate Rind, etc., add water and twice decoct them with the gruffs obtained after extracting the volatile oil, add 10 times water for the first time and add 8 times water for the second time, decoct for 2 hrs for each time, mix the decocted liquids and filter, mix the filtrate with the abovementioned aqueous solution and concentrate the mixed liquid to a relative density of 1.30 (determined at 50° C.), add Scorpion powder and clathrate of cyclodextrin thereto, decompress to condense (65° C.~75° C.) and dry the mixture, grind the dry mixture and add a proper amount of starch, mix them well, granulate with ethanol and dry the granules (lower than 60° C.), add 1% magnesium stearate and squash to 1000 tablets. The weight unit of the above raw materials is gram, the tablet specification is 0.4 g for each tablet, which corresponds to 1.79 g crude drug in whole.

Example 4

A preparation method of Chinese medicine tablet for treating AIDS is provided, wherein Chinese herbal medicines such as Geranium, Honeysuckle Flower, Pericarpium Trichosanthis, Root of Chinese Thorowax, Herb of Chinese Mosla, Pomegranate Rind, Root of Membranous Milkvetch, Liquorice Root, Flower of Common Bombax, Stem of Suberect Spatholobus, Safflower, Radix Oryzae, Fruit of Belleric Terminalia, Herba Hedyotis Diffusae, Fructus Trapae, Ginkgo leaf, Purslande herb, Rhizoma picrorhizae, Herba Solani Nigri, Scorpion are used as raw medicinal materials, and the preparation procedure is as follows:

A. Cut the medicinal materials (Geranium, Root of Chinese Thorowax, Herb of Chinese Mosla, and Honeysuckle Flower) for extracting volatile oil into 2-5 mm pieces, and grind fine powder medicinal material scorpion into fine powders for later use;

B. Extract the medicinal materials for extracting volatile oils for 5 hrs, collect the aqueous solution in another container after distillation. Clathrate the volatile oil with cyclodextrin for later use;

C. Add water and twice decoct the rest 15 medicinal materials such as Pomegranate Rind, etc. with the gruffs obtained after extracting the volatile oil, 10 times of water should be added for the first time and 8 times water for the second time, decoct them for 2 hrs for each time. Mix and filter (160-180 screen mesh) the decocted liquids, then mix the filtrate with the abovementioned aqueous solution, concentrate the mixture to a relative density about 1.30 (determined at 50° C.), add clathrate of fine scorpion powder and cyclodextrin, decompress to condense (65° C. 75° C.) till it is dry, grind the obtained substance and prepare powdered extract.

D. Add a proper amount of 16% wet starch to the powdered extract, mix well and add 95% ethanol, make granules through 16 mesh screen, then granulate through 14 mesh screen, dry (lower than 60° C.) and add 1% magnesium stearate, squash to 1000 tablets, and preparation is completed after tablets are coated.

The weight unit of the above raw materials is gram, the tablet specification is 0.4 g for each tablet, which corresponds to 1.79 g crude drug in whole.

Clinical observation of therapeutic effects of the invention:

The name of the tablet of the invention in the clinical trial is Xinxue Tablet, and in the following text we will use this name.

The test methods of the invention:

1. The test took random, double-blind, placebo parallel control, multicentre research method, the total therapeutic process of experimental treatment was 6 months. The screened and qualified patients would randomly take Xinxue tablet and placebo, and they would be visited in the zero, first, third and sixth month to evaluate the efficacy and safety of Xinxue tablet in treating HIV/AIDS.

One hundred and seventy-six clinically diagnosed HIV/AIDS patients were selected, and the clinical trial were carried out in five centers.

2. Patients Selection 2.1 Diagnosis standards: HIV infection classification and AIDS diagnosis standards revised by Centers for Disease Control and Prevention (CDC) of United States in 1993.

2.2 Selection Standard (1) Ages of patients were between 18 and 65 years old, male or female;

(2) HIV antibody was confirmed to be positive (W.B);

(3) CD4 cell counting was 100~400/μl (flow cytometry of BD company).

2.3 Treatment Discontinuation/Withdrawal Standards (1) Patients with severe adverse effects so that the observation could not be continued;

(2) Patients whose condition changes in observation so that the treatment must be changed;

(3) Patients who disobeyed the study plan or took contraindicated drugs;

(4) Patients who broke promises or loss visits.

2.4 Administration

The tested patients were randomly divided into a test group and a control group for 6 months' treatment. The drugs were all taken orally for thrice a day, and 8 tablets were swallowed down with warm water for each time. Raw, cold and spicy food should be avoided, and the drugs should be taken 2 hrs later if patients drink alcohol, the dose can not be changed.

3. Evaluation Criteria of Therapeutic Effects 3.1 Variables of Major Therapeutic Effects Comparison between absolute and relative changes of the values between CD4 cell counting and its baseline.

3.2 Variables of Secondary Therapeutic Effects (1) Changes of comparison between HIV load and the baseline;

(2) Changes of the ratio of CD4/CD8 before and after treatment;

(3) Changes of scores of body weight, clinical symptoms before and after treatment.

3.3 Evaluation Standards of Efficacy (1) Effective: increase in CD4 counting was more than 30% (including 30%);

(2) Ineffective: increase in CD4 counting was less than 30%.

4. Evaluation of Safety 4.1 Observation Variables of Safety (1) General medical examination items; (2) blood and urine routines; (3) hepatic and renal functions; (4) chest X-ray film, electrocardiogram, abdominal ultrasonic B.

4.2 Evaluation of Clinical Safety (1) Incidence of adverse drug event;

(2) Clinical safety should be evaluated according to the condition of adverse drug events obtained through patients' reports, researcher's observation or inquiry in a non-induced way.

Research Results of the Invention:

1. Case Distribution

One hundred and seventy-six patients were randomly assigned in groups, there were 88 patients in Xinxue tablet group and 88 patients in placebo group; 155 patients completed the trial and all the visits, in which 83 patients were in the Xinxue tablet group and 72 patients were in placebo group; 172 patients used the drug and experienced at least one safety evaluation, and they were listed in safe population; 171 patients used the drug and experienced at least one efficacy evaluation, and they were listed in ITT population; the 155 patients that completed cases were listed in PP population. ITT was the major study population.

2. Characters of demographic statistics: see table 1.

TABLE 1

Comparison of demographic character of selected patients (ITT)

| Item | Xinxue Tablet | Placebo | test statistics | P value |
|---|---|---|---|---|
| Sex: Male | 42(48.28%) | 36(42.86%) | 0.506($\chi^2$) | 0.4769 |
| Female | 45(51.72%) | 48(57.14%) | | |
| Mean age (age) | 39.23 | 38.44 | 0.379(F value) | 0.5390 |

TABLE 1-continued

Comparison of demographic character of selected patients (ITT)

| Item | Xinxue Tablet | Placebo | test statistics | P value |
|---|---|---|---|---|
| Mean stature (cm) | 163.93 | 162.55 | 1.991(F value) | 0.1601 |
| Mean weight (Kg) | 58.91 | 56.67 | 3.545(F value) | 0.0615 |

2. Evaluation of Therapeutic Effects 2.1 Analysis Results of Major Parameters of Therapeutic Effect 2.1.1 Changes of CD4 cell counting of two groups before and after treatment: comparison between changes of CD4 cell counting before treatment, 1, 3, 6 months after treatment, see table 2-1, 2-2.

TABLE 2-1

Comparison of CD4 cell counting changes of the two groups before and after treatment (/mm$^3$)

| | ITT | | PP | |
|---|---|---|---|---|
| Time | Xiexue tablet | Placebo | Xiexue tablet | placebo |
| baseline | | | | |
| Mean | 272.30 | 272.06 | 272.00 | 281.35 |
| 1 month | | | | |
| Mean | 292.68 | 294.60 | 292.67 | 299.74 |
| 3 months | | | | |
| Mean | 316.75 | 255.37 | 317.33 | 251.90 |
| 6 months | | | | |
| Mean | 345.15 | 251.60 | 347.10 | 248.50 |
| 6 months – baseline | | | | |
| Mean | 72.85 | −20.46 | 75.10 | −32.85 |

TABLE 2-2

Mean least square (LSMEANS) and 95% confidence interval of the value between CD4 cell counting of the two groups 6 months after treatment

| | | ITT | | | PP | | |
|---|---|---|---|---|---|---|---|
| Item "grouping" level and difference | | LSMean | 95% CIL | 95% CIU | LSMean | 95% CIL | 95% CIU |
| Changes of CD4 number | Xinxue Tablet | 69.32 | 55.70 | 82.93 | 71.64 | 60.81 | 82.47 |
| | Placebo | −24.56 | −38.66 | −10.46 | −37.38 | −49.28 | −25.48 |
| | Xinxue tablet – placebo | 93.88 | 76.29 | 111.46 | 109.02 | 95.04 | 123.00 |

It was demonstrated in the above results that, after 6 months' treatment, CD4 counting of the Xinxue tablet group increased and CD4 counting of the Placebo group decreased; it was demonstrated in the covariance analysis model that, the change of CD4 number was statistically significant (P<0.05). The variant values of the two groups were evaluated based on the model, in ITT population, the value of Xinxue tablet group increased 69.32 and the value of placebo group decreased 24.56, the results indicated that the effect of Xinxue tablet was superior to that of the placebo group.

2.1.2 Comparison of therapeutic effect of CD4: see table 3.

TABLE 3

Comparison of therapeutic effect of CD4 of the two groups

| time | ITT | | PP | |
|---|---|---|---|---|
| | Xinxue tablet | placebo | Xinxue tablet | placebo |
| 1 month | | | | |
| Effective | 15(17.24%) | 15(17.86%) | 14(16.87%) | 11(15.28%) |
| 3 months | | | | |
| Effective | 25(28.74%) | 6(7.14%) | 24(28.92%) | 3(4.17%) |
| 6 months | | | | |
| Effective | 44(50.57%) | 4(4.76%) | 43(51.81%) | 1(1.39%) |

Notes:
effective: CD4 counting increased more than 30% (including 30%);
ineffective: CD4 counting increased less than 30%.

It was demonstrated in the analytical results that, for the classification evaluation of therapeutic effects 6 months after treatment, the effective rate of Xinxue tablet group was obviously higher than that of the placebo group, and the difference of the therapeutic effect of the two groups was statistically significant (P<0.05).

2.2 Analytical Results of Variables of Secondary Therapeutic Effect 2.2.1 Comparison of changes of HIV load (log) of the two groups before treatment, 1, 3 and 6 months after treatment, see table 4-1, 4-2.

TABLE 4-1

Changes of HIV load (log) of the two groups before and after treatment

| | ITT | | PP | |
|---|---|---|---|---|
| Time | Xinxue tablet | placebo | Xinxue tablet | placebo |
| Baseline | | | | |
| Mean | 4.22 | 4.28 | 4.20 | 4.25 |
| 1 month | | | | |
| Mean | 4.14 | 4.12 | 4.13 | 4.11 |
| 3 months | | | | |
| Mean | 4.27 | 4.26 | 4.27 | 4.26 |
| 6 months | | | | |
| Mean | 4.22 | 4.54 | 4.22 | 4.61 |
| 6 months – baseline | | | | |
| Mean | 0.00 | 0.26 | 0.02 | 0.36 |

TABLE 4-2

Mean least square (LSMEANS) and 95% confidence interval of the value between HIV load (log) of the two groups 6 months after treatment

| | | ITT | | | PP | | |
|---|---|---|---|---|---|---|---|
| Item "grouping" level and difference | | LSMean | 95% CIL | 95% CIU | LSMean | 95% CIL | 95% CIU |
| Variance | Xinxue tablet | −0.05 | −0.20 | 0.09 | −0.05 | −0.19 | 0.10 |
| | Placebo | 0.21 | 0.06 | 0.36 | 0.29 | 0.13 | 0.45 |
| | Xiexue tablet – placebo | −0.27 | −0.45 | −0.08 | −0.34 | −0.52 | −0.15 |

It was demonstrated in the above results that, after 6 months' treatment, HIV load of Xinxue tablet was more or less the same as the value before treatment, while HIV load increased in the control group; it was demonstrated in the covariance analysis model that, the change of HIV load was statistically significant (P<0.05). The variant values of the two groups were evaluated based on the model, in ITT population, the value of Xinxue tablet group decreased 0.05 and the value of placebo group increased 0.21, the effect of Xinxue tablet was superior to that of the placebo group.

3.2.2 Changes of CD4/CD8 ratio of the two groups:

Six months after treatment, ratio of CD4/CD8 increased in the Xinxue tablet group, while the ratio decreased in the placebo group. In the covariance analysis model, it was demonstrated that the change of CD4/CD8 was statistically significant (P<0.05), and the Xinxue tablet was superior to the placebo group.

3.2.3 Total scale of clinical symptoms, body weight, diarrhea, poor appetite, fatigue, lipsotrichia and functional classification and its changes:

Total scale of clinical symptoms: the scale of Xinxue tablet decreased, while the scale of placebo increased, and the difference was statistically significant (P<0.05).

Body weight: body weight increased in Xinxue tablet group and decreased in placebo group. The Xinxue tablet group was better than the placebo group with a statistically significant difference (P<0.05).

Single clinical symptom: clinical symptoms of diarrhea, poor appetite, fatigue, lipsotrichia and functional classification, etc. were all obviously improved in Xinxue tablet group, and the difference was statistically significant (P<0.05) compared with the placebo group.

4 Safety Evaluation

Analyzing the conditions of patients with adverse reaction, and the results demonstrated that, the adverse reactions in treatment group were not all related with side effects of the drug. Through discussion and judgment, in the treatment group, one case had nausea and maldigestion, which were considered to be related with the administered drug; one case had insomnia, it happened after the drug had been administered for 2 months, but the symptom was light, the patient could still take the drug, and the adverse reaction might be related with the drug administered.

The examinations of hepatic function, renal function, blood routine, electrocardiogram, etc. were carried out for the tested patients before and after treatment, Xinxue tablet had no noticeable effect on the heart, liver, kidney functions and the blood routine, which demonstrated that Xinxue tablet was safe.

CONCLUSION

The efficacy and safety of Xinxue tablet for treating HIV/AIDS were evaluated by adopting random, double blind, placebo parallel control, multicentre clinical study, it was demonstrated by the results of clinical study that, Xinxue tablet had effects to significantly increase the CD4 cell counting, and it could significantly ameliorate the clinical symptoms of AIDS patients, increase the body weight of the patients and the ratio of CD4/CD8, and it probably postponed the replication of HIV. No obvious toxic or adverse effect was observed in the clinical trial.

The invention claimed is:

1. A medicine preparation, characterized in that the preparation is prepared according to the following weight unit of raw medicinal materials:

| | |
|---|---|
| Geranium | 120-150 unit |
| Root of Membranous Milkvetch | 120-150 unit |
| Herba Solani Nigri | 120-200 unit |
| Honeysuckle Flower | 120-200 unit |
| Flower of Common Bombax | 60-100 unit |
| Fruit of Belleric Terminalia | 40-60 unit |
| Herba Hedyotis Diffusae | 80-150 unit |
| Pomegranate Rind | 40-60 unit |
| Radix Oryzae | 150-200 unit |
| Fructus Trapae | 80-150 unit. |

2. The medicine preparation according to claim 1, characterized in that the preparation is prepared according to the following weight unit of raw medicinal materials:

| | |
|---|---|
| Geranium | 180 unit |
| Root of Membranous Milkvetch | 180 unit |
| Herba Solani Nigri | 180 unit |
| Honeysuckle Flower | 180 unit |
| Flower of Common Bombax | 120 unit |
| Fruit of Belleric Terminalia | 90 unit |
| Herba Hedyotis Diffusae | 180 unit |
| Pomegranate Rind | 90 unit |
| Radix Oryzae | 300 unit |
| Fructus Trapae | 180 unit. |

3. The medicine preparation according to claim 1, characterized in that the preparation is prepared according to the following weight unit of raw materials:

| | |
|---|---|
| Geranium | 120-150 unit |
| Root of Membranous Milkvetch | 120-150 unit |
| Herba Solani Nigri | 120-120 unit |
| Honeysuckle Flower | 120-120 unit |
| Flower of Common Bombax | 60-100 unit |
| Fruit of Belleric Terminalia | 40-60 unit |
| Herba Hedyotis Diffusae | 80-150 unit |
| Pomegranate Rind | 40-60 unit |
| Radix Oryzae | 150-200 unit |
| Fructus Trapae | 80-150 unit |
| Pericarpium Trichosanthis | 40-60 unit |
| Root of Chinese Thorowax | 60-100 unit |
| Herb of Chinese Mosla | 40-60 unit |
| Liquorice Root | 60-80 unit |
| Stem of Suberect Spatholobus | 120-150 unit |
| Safflower | 40-60 unit |
| Ginkgo leaf | 40-60 unit |
| Purslane herb | 60-120 unit |
| Rhizoma picrorhizae | 40-60 unit |
| Scorpion | 28-40 unit. |

* * * * *

UNITED STATES PATENT AND TRADEMARK OFFICE
CERTIFICATE OF CORRECTION

PATENT NO.         : 7,381,430 B2                                      Page 1 of 1
APPLICATION NO. : 10/599758
DATED              : June 3, 2008
INVENTOR(S)        : Zuqin Lai et al.

It is certified that error appears in the above-identified patent and that said Letters Patent is hereby corrected as shown below:

On the line 45 of the column 12 of the patent grant, please replace the phrase "Herba Solani Nigri   120-120 unit" with -- Herba Solani Nigri   120-200 unit --

On the line 46 of the column 12 of the patent grant, please replace the phrase "Honeysuckle Flower   120-120 unit" with -- Honeysuckle Flower   120-200 unit --

Signed and Sealed this

Third Day of February, 2009

JOHN DOLL
*Acting Director of the United States Patent and Trademark Office*